(12) United States Patent
Matsumori

(10) Patent No.: US 7,902,261 B2
(45) Date of Patent: Mar. 8, 2011

(54) MEDICINAL COMPOSITIONS FOR PREVENTING OR TREATING VIRAL MYOCARDITIS

(75) Inventor: Akira Matsumori, Minoh (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 484 days.

(21) Appl. No.: 11/139,532

(22) Filed: May 31, 2005

(65) Prior Publication Data

US 2005/0234133 A1      Oct. 20, 2005

Related U.S. Application Data

(63) Continuation of application No. 10/019,263, filed as application No. PCT/JP00/04286 on Jun. 28, 2000, now abandoned.

(30) Foreign Application Priority Data

Jun. 30, 1999   (JP) ................................ 1999-185297

(51) Int. Cl.
*A01N 33/18*       (2006.01)
*A01N 33/24*       (2006.01)
(52) U.S. Cl. ...................................................... 514/727
(58) Field of Classification Search .................. 514/726, 514/727

See application file for complete search history.

(56) References Cited

U.S. PATENT DOCUMENTS

| 5,604,229 | A | 2/1997 | Fujita et al. |
| 6,277,888 | B1 | 8/2001 | Sakai et al. |
| 6,476,004 | B1 | 11/2002 | Sakai et al. ....................... 514/58 |

FOREIGN PATENT DOCUMENTS

| EP | 1 050 301 | 11/2000 |
| JP | WO98/03162 | 1/1998 |
| WO | 94/08943 | 4/1994 |
| WO | 98/03162 | 1/1998 |
| WO | 98/37875 | 9/1998 |
| WO | 99/36065 | 7/1999 |

OTHER PUBLICATIONS

The Merck Manual, 16th ed., 1992, pp. 2370-2371.

*Primary Examiner* — San-ming Hui
(74) *Attorney, Agent, or Firm* — Wenderoth, Lind & Ponack, L.L.P.

(57) ABSTRACT

The present invention aims at providing a pharmaceutical composition for the prophylaxis or treatment, irrespective of the kind of virus, of viral myocarditis or viral diseases induced by viral myocarditis, by the treatment or prevention of the onset of cytotoxicity in various organs, and a method of the prophylaxis or treatment. The present invention also relates to a pharmaceutical composition for the prophylaxis or treatment of viral myocarditis or viral diseases induced by viral myocarditis, which contains 2-amino-2-(2-(4-octylphenyl)ethyl)propane-1,3-diol or a pharmacologically acceptable salt thereof as an active ingredient. The present invention further relates to a method for the prophylaxis or treatment of viral myocarditis or viral diseases induced by viral myocarditis, which includes administering an effective amount of the aforementioned compound or a pharmacologically acceptable salt thereof.

4 Claims, 6 Drawing Sheets

MEDICINAL COMPOSITIONS FOR PREVENTING OR TREATING VIRAL MYOCARDITIS This application is a continuation of Ser. No. 10/019,263 filed Dec. 28, 2001, now abandoned, which is a U.S. national stage of International Application No. PCT/JP00/04286 filed Jun. 28, 2000.

TECHNICAL FIELD

The present invention relates to a pharmaceutical composition for the prophylaxis and treatment of viral myocarditis or viral diseases induced by viral myocarditis, which composition comprises 2-amino-2-(2-(4-octylphenyl)-ethyl)propane-1,3-diol or a pharmacologically acceptable salt thereof as an active ingredient. More particularly, the present invention relates to a pharmaceutical composition for the amelioration and prophylaxis of viral cytotoxicity. The present invention also relates to a method for the prophylaxis or treatment of viral myocarditis or viral diseases induced by viral myocarditis, which method comprises administering 2-amino-2-(2-(4-octylphenyl)ethyl)propane-1,3-diol or a pharmacologically acceptable salt thereof. The present invention further relates to use of 2-amino-2-(2-(4-octylphenyl)ethyl)propane-1,3-diol or a pharmacologically acceptable salt thereof for the production of a pharmaceutical agent for the prophylaxis and treatment of viral myocarditis or viral diseases induced by viral myocarditis.

BACKGROUND ART

Conventionally, viral diseases have been mainly prevented by the use of virus vaccines. However, vaccines are made specifically for individual viruses and are effective only for such individual viruses. There are numerous kinds of viruses, whereas vaccines are currently put to use against a very limited number of viruses. Moreover, viruses often include many mutant strains, but a vaccine effective against one virus often may not be so against a different virus of the same kind. In addition, it is extremely difficult to develop many vaccines associated with fewer side effects.

On the other hand, various antiviral agents (acyclovir, ganciclovir, Ara-A etc.) have been developed and put to use, but they are effective against an extremely narrow range of viral infections, and there has been found no drug effective against a broad range of viral diseases. These antiviral agents show strong side effects, which prevents general application thereof in clinical situations. In recent years, interferon has been applied to the treatment of viral hepatitis and the like, but side effects, such as fever, occur frequently. While interferon inhibits growth of viruses, there have been found no reports on the direct prevention of cytotoxicity. Gamma globulin has been widely used for the treatment of viral diseases, but its achievement is not necessarily consistent.

2-Aminopropane-1,3-diol compounds including 2-amino-2-(2-(4-octylphenyl)ethyl)propane-1,3-diol hydrochloride are known as a suppressant of rejection in organ or bone marrow transplantation, and as a therapeutic agent of various autoimmune diseases (e.g., psoriasis, Behcet's disease) and rheumatic diseases (WO94/08943).

However, the prior art has never acknowledged effectiveness of a 2-aminopropane-1,3-diol compound for the treatment of viral diseases.

DISCLOSURE OF THE INVENTION

As mentioned above, there are numerous kinds of viruses and a specific treatment against each virus is not feasible. Therefore, the prophylaxis and treatment of cytotoxicity in various organs, that occurs in many viral diseases, is extremely significant. The cytotoxicity in viral diseases is considered to be caused by direct injury due to the growth of viruses and various immunoreactions induced by viral infections. The present invention aims at the prophylaxis and treatment, irrespective of the kind of virus, of viral myocarditis and viral diseases induced by viral myocarditis, by the treatment and prevention of the onset of cytotoxicity in various organs.

The present inventor has conducted intensive studies of a pharmaceutical agent for the prophylaxis and treatment of viral myocarditis and viral diseases induced by viral myocarditis, in an attempt to solve the above-mentioned problems, and surprisingly found that 2-amino-2-(2-(4-octylphenyl)ethyl)propane-1,3-diol and a pharmacologically acceptable salt thereof are effective, which resulted in the completion of the present invention.

Accordingly, the present invention provides the following.
(1) A pharmaceutical composition for the prophylaxis or treatment of viral myocarditis, which contains 2-amino-2-(2-(4-octylphenyl)ethyl)propane-1,3-diol or a pharmacologically acceptable salt thereof, and a pharmaceutically acceptable carrier.
(2) A pharmaceutical composition for the prophylaxis or treatment of viral diseases induced by viral myocarditis, which contains 2-amino-2-(2-(4-octylphenyl)ethyl)propane-1,3-diol or a pharmacologically acceptable salt thereof, and a pharmaceutically acceptable carrier.
(3) A pharmaceutical composition for the amelioration or prophylaxis of viral cytotoxicity, which contains 2-amino-2-(2-(4-octylphenyl)ethyl)propane-1,3-diol or a pharmacologically acceptable salt thereof, and a pharmaceutically acceptable carrier.
(4) A method for the prophylaxis or treatment of viral myocarditis, which comprises administering an effective amount of 2-amino-2-(2-(4-octylphenyl)ethyl)propane-1,3-diol or a pharmacologically acceptable salt thereof.
(5) A method for the prophylaxis or treatment of viral diseases induced by viral myocarditis, which comprises administering an effective amount of 2-amino-2-(2-(4-octylphenyl)ethyl)propane-1,3-diol or a pharmacologically acceptable salt thereof.
(6) A method for the amelioration or prophylaxis of viral cytotoxicity, which comprises administering an effective amount of 2-amino-2-(2-(4-octylphenyl)ethyl)propane-1,3-diol or a pharmacologically acceptable salt thereof.
(7) Use of 2-amino-2-(2-(4-octylphenyl)ethyl)propane-1,3-diol or a pharmacologically acceptable salt thereof for the production of a pharmaceutical agent for the prophylaxis or treatment of viral myocarditis.
(8) Use of 2-amino-2-(2-(4-octylphenyl)ethyl)propane-1,3-diol or a pharmacologically acceptable salt thereof for the production of a pharmaceutical agent for the prophylaxis or treatment of viral diseases induced by viral myocarditis.
(9) Use of 2-amino-2-(2-(4-octylphenyl)ethyl)propane-1,3-diol or a pharmacologically acceptable salt thereof for the production of a pharmaceutical agent for the amelioration or prophylaxis of viral cytotoxicity.
(10) A commercial package comprising the pharmaceutical composition of (1) and a written matter associated therewith, the written matter stating that the pharmaceutical composition can or should be used for the prophylaxis or treatment of viral myocarditis.
(11) A commercial package comprising the pharmaceutical composition of (2) and a written matter associated therewith, the written matter stating that the pharmaceutical composition can or should be used for the prophylaxis or treatment of viral diseases induced by viral myocarditis.

(12) A commercial package comprising the pharmaceutical composition of (3) and a written matter associated therewith, the written matter stating that the pharmaceutical composition can or should be used for the amelioration or prophylaxis of viral cytotoxicity.

In the present invention, viral myocarditis and viral diseases induced by viral myocarditis are preferably those induced by RNA virus or hepatitis virus. In the context of the present invention, the above-mentioned RNA virus is preferably orthomyxovirus or picornavirus. According to the present invention, the aforementioned viral diseases are preferably viral hepatitis (type A, type B, type C, type E, type G and type TTV), adenovirus infection, influenza, herpes infection, viral encephalitis, cytomegalovirus infection, viral enteritis and viral pericarditis.

DETAILED DESCRIPTION OF THE INVENTION

Figure 1:
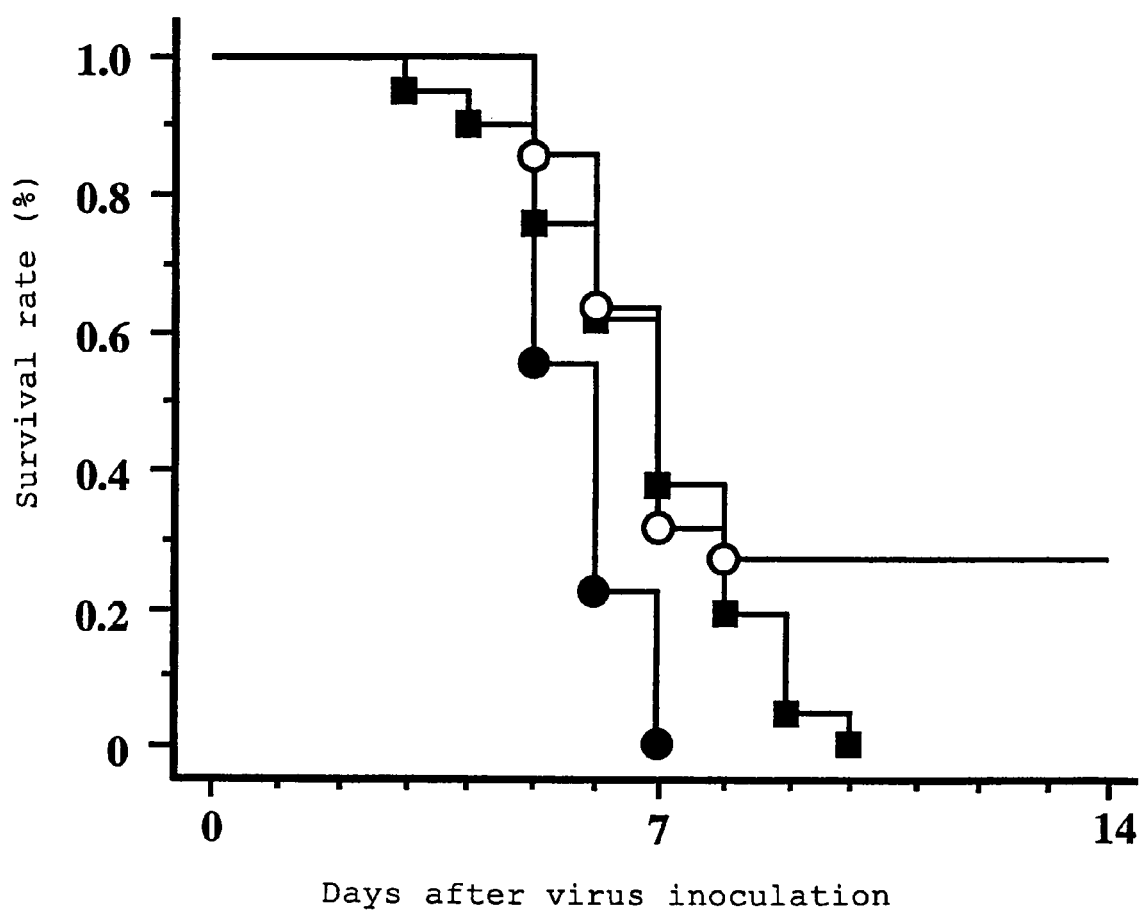
FIG. 1 shows survival rates in Experimental Example 2, wherein -■- shows a control group, -●- shows a CsA group, and -○- shows a compound 1 group.

The 2-amino-2-(2-(4-octylphenyl)ethyl)propane-1,3-diol in the present invention is a known compound and can be produced by, for example, a method disclosed in WO94/08943.

The 2-amino-2-(2-(4-octylphenyl)ethyl)propane-1,3-diol can be converted to a pharmacologically acceptable salt, such as salts with the following acids, by treating with an acid (e.g., hydrochloric acid, hydrobromic acid, hydroiodic acid, sulfuric acid, nitric acid, phosphoric acid, acetic acid, maleic acid, fumaric acid, benzoic acid, citric acid, oxalic acid, succinic acid, tartaric acid, malic acid, mandelic acid, methanesulfonic acid, benzenesulfonic acid, p-toluenesulfonic acid, 10-camphorsulfonic acid and the like) in, where necessary, a suitable solvent such as water, methanol, ethanol, diethyl ether, tetrahydrofuran, dioxane and the like.

In the present invention, 2-amino-2-(2-(4-octylphenyl)-ethyl)propane-1,3-diol and a pharmacologically acceptable salt thereof are low toxic and are useful as a pharmaceutical agent for the prophylaxis and treatment of viral myocarditis and viral diseases induced thereby in animals, particularly mammals (e.g., human, dog, rabbit, mouse, rat and the like). The viral myocarditis and viral diseases induced thereby to be the target in the present invention include the diseases caused by pathogenic viruses belonging to DNA virus or RNA virus. Such pathogenic virus is exemplified in the following.

DNA virus: poxvirus, herpesvirus (herpes simplex virus, cytomegalovirus, EB virus etc), adenovirus, parvovirus RNA virus: reovirus, togavirus, coronavirus, rhabdovirus, paramyxovirus, orthomyxovirus, bunyavirus, arenavirus, retrovirus, picornavirus, calicivirus In particular, the pharmaceutical agent of the present invention can be preferably applied to the treatment and prophylaxis of viral myocarditis caused by the RNA virus or hepatitis virus and viral diseases induced thereby. As used herein, examples of the RNA virus include orthomyxovirus and picornavirus.

The viral diseases induced by viral myocarditis are specifically exemplified by viral hepatitis (type A, type B, type C, type E, type G, type TTV), adenovirus infection, influenza, viral pneumonia, viral bronchitis, herpes infection (herpes simplex, EB virus (infectious mononucleosis, herpes zoster), poliomyelitis, AIDS (HIV infection), adult T cell leukemia (ATL), papilloma, measles, rubella, roseola infantum, erythema infectiosum, viral encephalitis, viral meningitis, cytomegalovirus infection, epidemic parotitis, chickenpox, rabies, viral enteritis, viral pericarditis, coxsackievirus infection, echovirus infection, hemorrhagic fever with renal syndrome, Lassa fever and the like.

Of the viral diseases mentioned above, the present invention can be preferably applied to viral hepatitis (type A, type B, type C, type E, type G, type TTV), adenovirus infection, influenza, herpes infection, viral encephalitis, cytomegalovirus infection, viral enteritis and viral pericarditis.

2-Amino-2-(2-(4-octylphenyl)ethyl)propane-1,3-diol and a pharmacologically acceptable salt thereof can be used orally or parenterally by inhalation, rectal administration or local administration as a pharmaceutical product composition or a preparation (e.g., powder, granule, tablet, pill, capsule, injection, syrup, emulsion, elixir, suspension, solution and the like). 2-Amino-2-(2-(4-octylphenyl)ethyl)propane-1,3-diol and a pharmacologically acceptable salt thereof of the present invention may be used alone or by admixing with a pharmaceutically acceptable carrier (adjuvant, excipient, vehicle and/or diluent and the like). The pharmaceutical composition can be formulated into a preparation according to a conventional method.

In the present specification, by parenterally is meant subcutaneous injection, intravenous injection, intramuscular injection, intraperitoneal injection, infusion and the like. A preparation for injection, such as sterile aqueous suspension or oily suspension for injection, can be prepared using a suitable dispersing agent, moistening agent or suspending agent according to a method known in the pertinent field. The sterile preparation for injection may be a sterile and injectable solution or suspension in a parenterally administrable diluent or solvent, such as aqueous solution and the like, which is acceptable for the formulation of preparations. The usable vehicle or solvent may be, for example, water, Ringer solution, isotonic saline and the like. In addition, sterile non-volatile oil can be used as a solvent or suspending medium. Any non-volatile oil, fatty acid, natural or synthetic or semi-synthetic fatty oil or fatty acid, natural or synthetic or semi-synthetic mono-, di- or triglyceride for this end is encompassed.

The suppository for rectal administration can be produced by admixing the drug and a suitable less irritant vehicle, such as cacao butter and polyethylene glycol, which is solid at normal temperature but liquid at the temperature of intestine, and which melts in the rectum to release the drug, and the like.

The solid dosage form for oral administration may be the above-mentioned powder, granule, tablet, pill, capsule and the like. In such a dosage form, the active ingredient compound can be mixed with at least one additive, such as sucrose, lactose, cellulose sugar, mannitol, maltitol, dextran, starches, agar, alginate, chitin, chitosan, pectin, tragacanth, gum arabic, gelatin, collagen, casein, albumin, synthetic or semi-synthetic polymer or glyceride. Such dosage form may contain a different additive as does a typical dosage form. The different additive includes, for example, inert diluent, lubricant such as magnesium stearate and the like, preservative such as parahydroxybenzoate, sorbic acid and the like, antioxidant such as ascorbic acid, α-tocopherol, cysteine and the like, disintegrant, binder, thickener, buffer, sweetener, flavor, perfume and the like. The tablet and pill may be enteric coated.

The liquid for oral administration may be, for example, pharmaceutically acceptable syrup, emulsion, elixir, suspension, solution and the like. These may contain an inert diluent typically used in the pertinent field, such as water.

The dose for a specific patient is determined according to age, body weight, general health state, sex, diet, administration time, administration method, clearance rate, combination of drugs, the condition for which the patient is undergoing treatment, and other factors. 2-Amino-2-(2-(4-octylphenyl)ethyl)propane-1,3-diol and a pharmacologically acceptable salt thereof are low toxic and can be used safely. While the daily dose of the compound varies depending on the condition and body weight of the patient, administration route and the like, when it is orally administered as a pharmaceutical agent for the treatment of viral myocarditis or viral diseases induced by viral myocarditis in adult, the daily dose is approximately 0.01-150 mg, preferably 0.1-100 mg, and approximately 0.01-50 mg, preferably 0.01-20 mg, by intravenous injection, which is preferably administered in one, two or three doses.

EXAMPLES

The effect of the present invention is clarified in the following by referring to Experimental Examples. These examples are for mere exemplification and the present invention is not limited in any way by these examples.

Experimental Example 1

Effect on Viral Myocarditis

Compound 1: 2-Amino-2-(2-(4-octylphenyl)ethyl)propane-1,3-diol hydrochloride (1) Survival Rate
Method
Four-week-old DBA/2 mice were divided into 3 groups, and EMC (Encephalomyocarditis) virus (10 pfu) was intraperitoneally inoculated. After inoculation, distilled water (solvent, group A, n=11) as a control, compound 1 (1 mg/kg/day, group B, n=10), and compound 1 (3 mg/kg/day, group C, n=10) were orally administered forcibly for 14 consecutive days using a probe. The survival rate of each group after 14 days was compared by Kaplan-Meier method.
Results
The mice in the control group (group A, n=11) all died by day 8 (survival rate 0%) but the survival rate of the compound 1 administration group at day 14 was one mouse for group B (n=10, survival rate 10%), and 3 mice for group C (n=10, survival rate 30%). In the 3 mg/kg/day group, a statistically significant improvement in the survival rate was observed (p<0.05).

(2) Histopathological Observation of the Heart
Method
Four-week-old DBA/2 mice were divided into 3 groups and EMC (Encephalomyocarditis) virus (10 pfu) was intraperitoneally inoculated. After inoculation, distilled water (solvent, n=9) as a control, compound 1 (3 mg/kg/day, n=8), and compound 1 (10 mg/kg/day, n=8) were orally administered forcibly for 5 consecutive days using a probe. Five days later, the heart was removed, and, after fixing with formalin, subjected to hematoxylin-eosin staining, based on which heart necrosis and cellular infiltration were scored as follows.
0; no lesion,
1+; lesion in 25% or less of the heart,
2+; lesion in more than 25% and not more than 50% of the heart
3+; lesion in more than 50% and not more than 75% of the heart
4+; lesion in more than 75% and not more than 100% of the heart
Results
The results of the histopathological observation of the heart are shown in Table 1.

TABLE 1

|  | necrosis of myocardial cell | cellular infiltration* |
| --- | --- | --- |
| control group | 1.9 ± 0.2 | 2.0 ± 0.2 |
| 3 mg/kg/day administration group | 1.7 ± 0.4 | 1.6 ± 0.2 |
| 10 mg/kg/day administration group | 1.0 ± 0.2* | 1.1 ± 0.2* | mean ± SEM, *p < 0.05 (vs. control group)

From Table 1, it is evident that the myocardial cell necrosis and cellular infiltration of the heart were improved dose dependently in the 10 mg/kg/day administration group at 5 days after the EMC virus inoculation.

From the above results, 2-amino-2-(2-(4-octylphenyl)-ethyl)propane-1,3-diol hydrochloride was found to improve the mortality rate of the mice by EMC viral infection, ameliorate viral myocarditis and prove effective against viral infection.

The animal model of the above-mentioned dilated cardiomyopathy is described in Circulation. 65:1230-1235, 1982 and Circulation. 66:355-360, 1982.

Experimental Example 2

The effects on viral myocarditis of compound 1 and an immunosuppressant, cyclosporin A (hereinafter to be referred to as CsA), were compared. The compound 1 was dissolved in sterile distilled water and administered, and CsA was dissolved in olive oil and administered.
(1) Survival Rate
Method
Four-week-old DBA/2 male mice were divided into 3 groups, and EMC virus (10 pfu) was intraperitoneally inoculated. After inoculation, distilled water (solvent, control group, n=21), CsA (40 mg/kg/day, CsA group, n=9), and compound 1 (10 mg/kg/day, compound 1 group, n=22) were orally administered forcibly for 14 consecutive days using a probe. The survival rate of each group after 14 days was compared by Kaplan-Meier method.

Results

The results are shown in FIG. 1. The mice in the control group (-■-) all died by day 10 (survival rate 0%). The mice in the CsA group (-●-) all died by day 7, and the survival rate dropped significantly as compared to the control group. In contrast, the survival rate of the compound 1 group (-○-) at day 14 was 27% (6 out of 22 survived). A significant difference was found in the survival rates between the CsA group and the control group (*p<0.05).

(2) Histopathological Observation of the Heart

Method

Four-week-old male DBA/2 mice were divided into 3 groups and EMC virus (10 pfu) was intraperitoneally inoculated. After inoculation, distilled water (solvent, n=9) as a control, CsA (40 mg/kg/day, n=6), and compound 1 (10 mg/kg/day, n=8) were orally administered forcibly for 5 consecutive days using a probe. Five days later, the heart was harvested, and, after fixing with formalin, subjected to hematoxylin-eosin staining, based on which heart necrosis and cellular infiltration were scored according to the criteria shown in Experimental Example 1.

The myocardial cell necrosis and cellular infiltration were independently scored by two observers and averaged. The statistical analysis was performed by one way analysis of variance (ANOVA) and Fisher's protected least significant difference test.

Results

Figure 2:
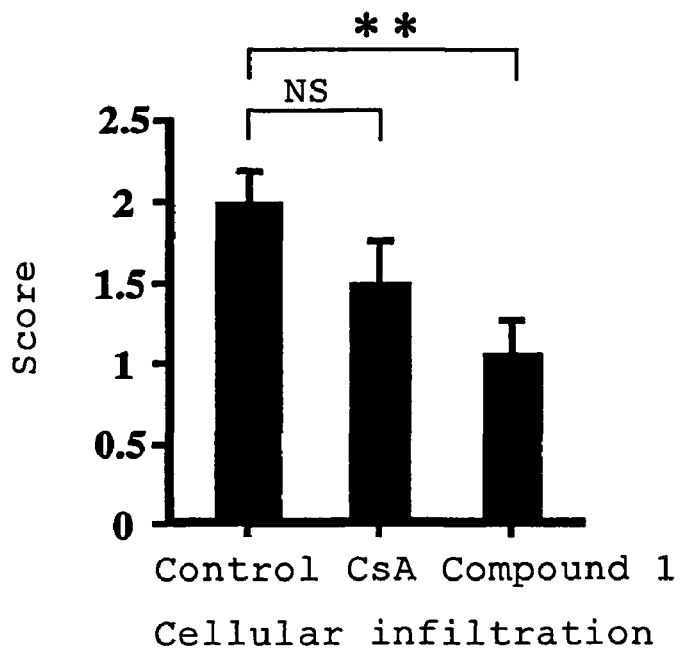
FIG. 2 is a graph showing the cellular infiltration score in Experimental Example 2.
Figure 3:
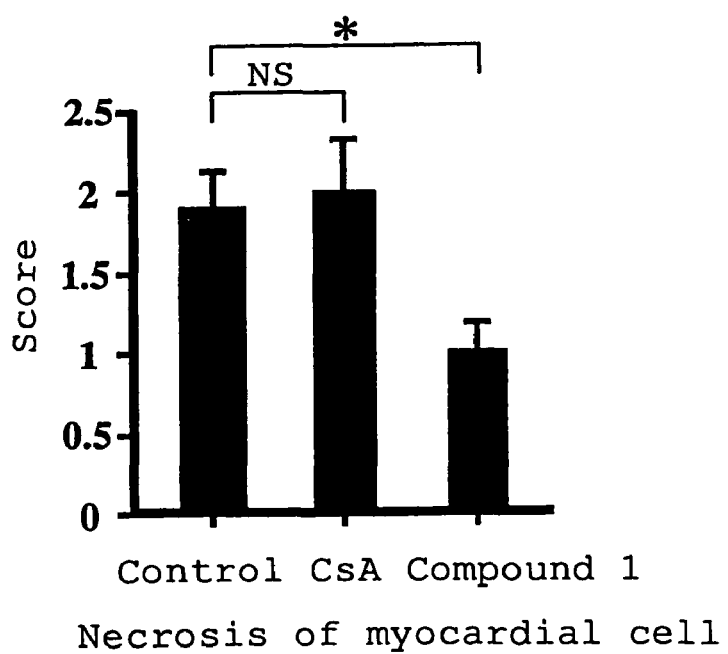
FIG. 3 is a graph showing the myocardial cell necrosis score in Experimental Example 2.

The results are shown in FIG. 2 (cellular infiltration), FIG. 3 (necrosis of myocardial cell) and Table 2.

TABLE 2

|  | cellular infiltration | necrosis of myocardial cell |
| --- | --- | --- |
| control group | 2.00 ± 0.19 | 1.89 ± 0.23 |
| CsA group | 1.50 ± 0.26(NS) | 2.00 ± 0.32(NS) |
| compound 1 group | 1.06 ± 0.19** | 1.00 ± 0.19* | mean ± SEM, NS: no significant difference, **p < 0.01, *p < 0.05 (vs. control group)

While the score of cellular infiltration in the CsA group was lower than that of the control group, no significant difference was found. While the score of myocardial cell necrosis in the CsA group was slightly higher than that of the control group, no significant difference was found. In contrast, the scores of both cellular infiltration and myocardial cell necrosis were significantly lower in the compound 1 group than in the control group. Therefore, a significant ameliorating effect on myocardial cell necrosis and cellular infiltration was found by the administration of compound 1.

(3) Intracardiac Virus Titer

Method

Four-week-old male DBA/2 mice were divided into 3 groups and EMC virus (10 pfu) was intraperitoneally inoculated. After inoculation, distilled water (solvent, n=8) as a control, CsA (40 mg/kg/day, n=5), and compound 1 (10 mg/kg/day, n=7) were orally administered forcibly for 5 consecutive days using a probe. Five days later, the heart was aseptically harvested from the mice, and after weighing the ventricle, homogenized in phosphate-buffered saline (PBS, 1 ml). The homogenate was centrifuged at 4° C., 1,500 g for 15 min and the supernatant (0.1 ml) was inoculated to human amnion FL cell monolayer and cultured at 37° C. for 60 min in 5% $CO_2$. The cells were overlaid with a medium (3 ml) containing 4% fetal calf serum and 1% methylcellulose. After culture under 5% $CO_2$-containing humidified atmosphere at 37° C. for 20 hr, the cells were fixed with acetic acid-methanol (1:2) and stained with 1% crystal violet. The plaques were counted under an inverted microscope (Circulation. 89:846-851, 1994). When the plaques are too many to count, the supernatant is appropriately diluted with Dulbecco's modified Eagle's medium (DMEM) and subjected to a similar assay. The test was repeated and the mean was taken. The virus titer was expressed in pfu/g heart. The statistical analysis was conducted by one way ANOVA and Fisher's protected least significant difference test.

Results

Figure 4:
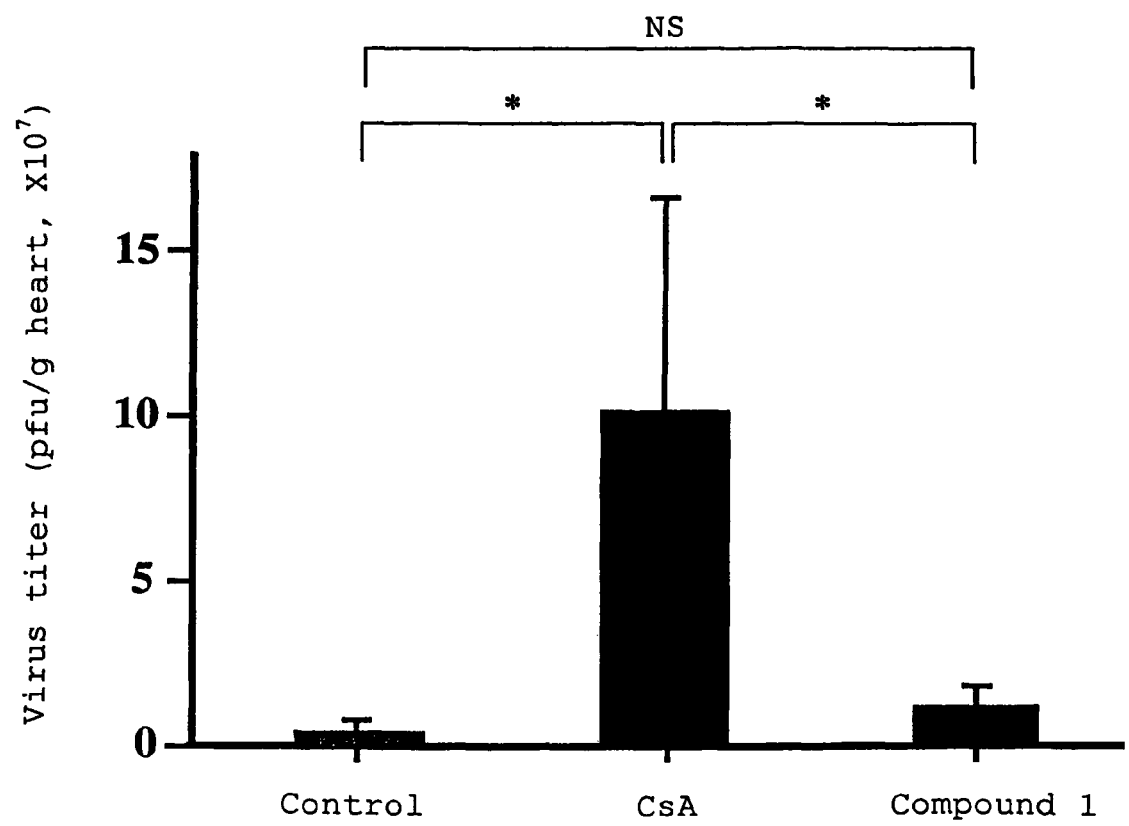
FIG. 4 is a graph showing the intracardiac virus titer in Experimental Example 2.
Figure 5:
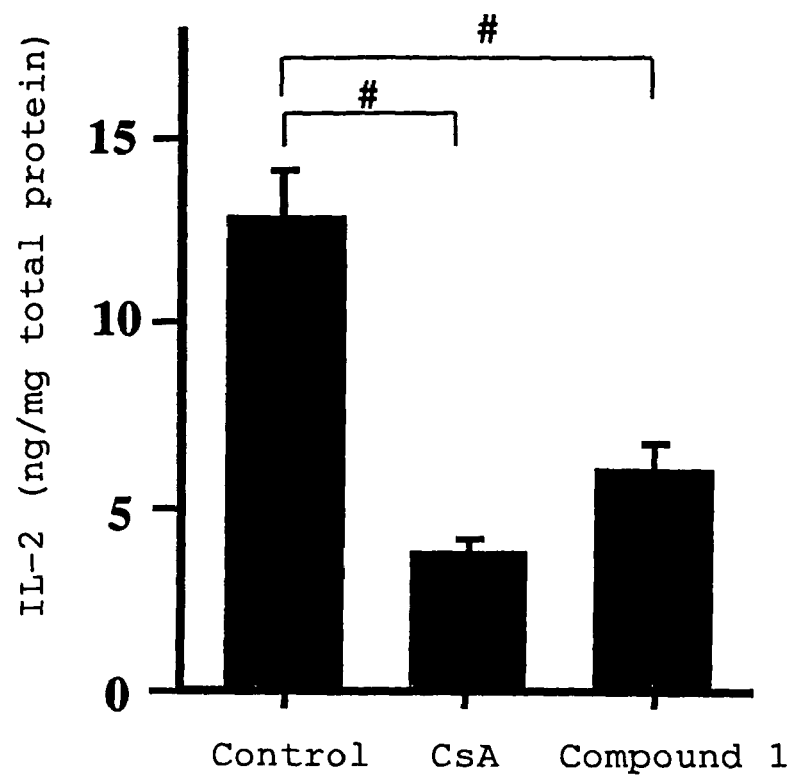
FIG. 5 is a graph showing the results of the intracardiac cytokine assay of IL-2 in Experimental Example 2.
Figure 6:
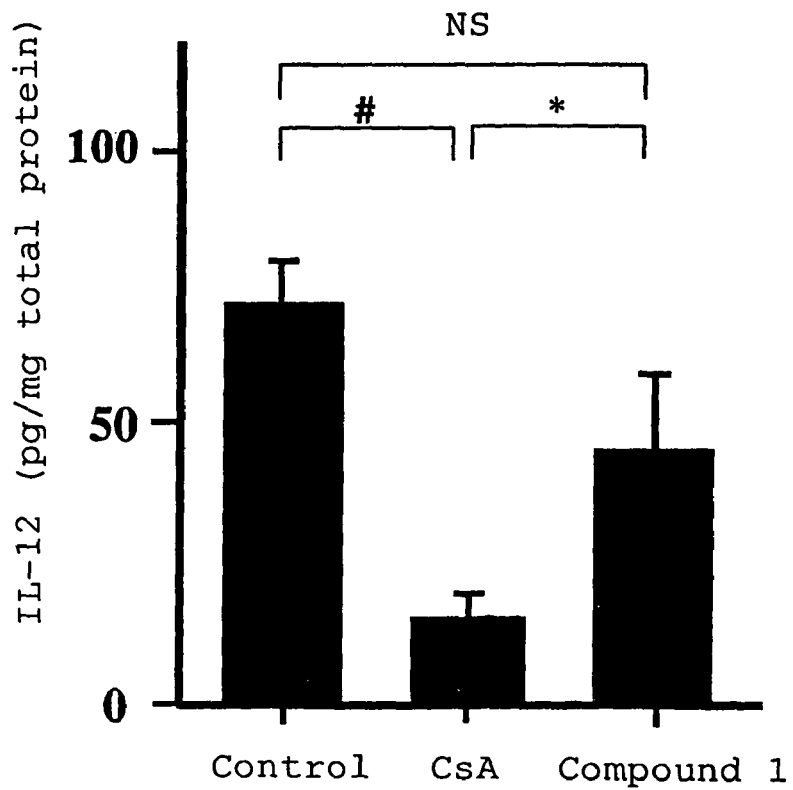
FIG. 6 is a graph showing the results of the intracardiac cytokine assay of IL-12 in Experimental Example 2.
Figure 7:
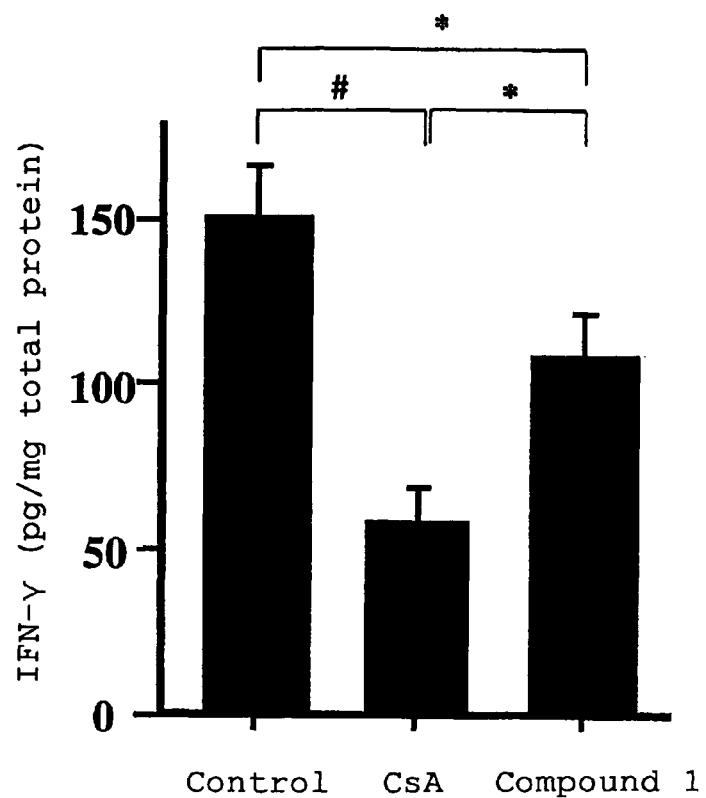
FIG. 7 is a graph showing the results of the intracardiac cytokine assay of IFN-γ in Experimental Example 2.
Figure 8:
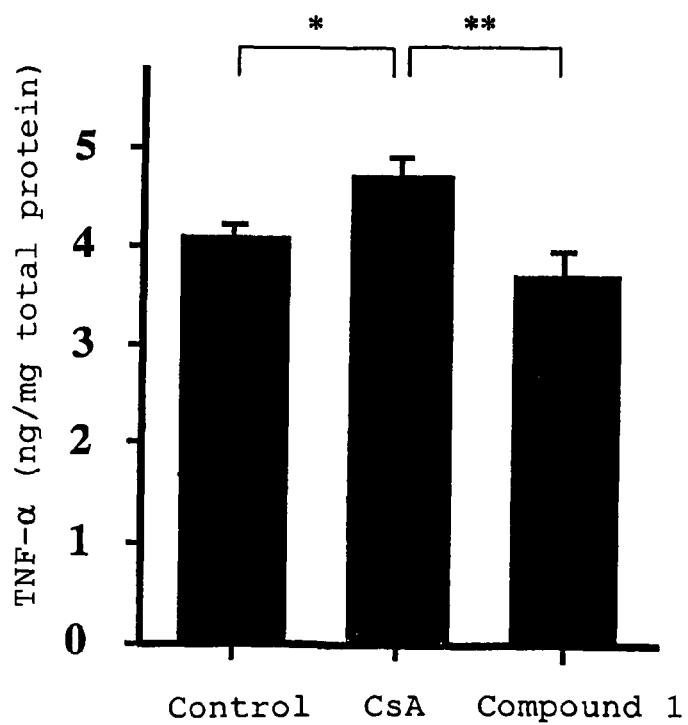
FIG. 8 is a graph showing the results of the intracardiac cytokine assay of TNF-α in Experimental Example 2.

The results are shown in FIG. 4 and Table 3.

TABLE 3

|  | virus titer (pfu/g heart) |
| --- | --- |
| control group | $5.18 ± 2.73 × 10^6$ |
| CsA group | $9.94 ± 6.30 × 10^{7*}$ |
| compound 1 group | $1.23 ± 0.53 × 10^7$ (NS) | mean ± SEM, NS: no significant difference, *p < 0.05 (vs. control group)

CsA increased virus replication in the heart by about 20 times as compared to the control group. In contrast, compound 1 showed no effect of increase in virus replication, unlike CsA.

(4) Intracardiac Cytokine Assay

Method

The ventricle of the mice, harvested in the above-mentioned (3) at day 5, was homogenized in PBS (1 ml) using an ultrasonic homogenizer and centrifuged at 4° C., 14,000 rpm for 20 min. The supernatant was used as the samples for the IL-2, IL-12, IFN-γ and TNF-α assay. The protein concentration of each cytokine was assayed by ELISA using a commercially available kit (Circulation. 100:1102-1108, 1999). The ELISA kits for the mouse IL-2 and IFN-γ were purchased from GENZYME Corporation, Cambridge, U.S.A. and the ELISA kits for mouse IL-12 and TNF-α were purchased from ENDOGEN Inc., Cambridge, U.S.A.

The total protein concentration of each supernatant was measured by bicinchoninic acid (BCA) method, and the ratio of the cytokine concentration to the total protein concentration was calculated (J. Am. Coll. Cardiol. 33:1400-1407, 1999). Each cytokine protein concentration was expressed in pg/mq total protein or ng/mg total protein. The statistical analysis was conducted by one way ANOVA and Fisher's protected least significant difference test.

Results

The results are shown in FIGS. 5-8 and Table 4.

TABLE 4

|  | IL-2 (ng/mg total protein) | IL-12 (pg/mg total protein) | IFN-γ (pg/mg total protein) | TNF-α (ng/mg total protein) |
| --- | --- | --- | --- | --- |
| control group | 12.79 ± 1.24 | 71.76 ± 7.37 | 151.20 ± 15.66 | 4.11 ± 0.11 |

TABLE 4-continued

|  | IL-2 (ng/mg total protein) | IL-12 (pg/mg total protein) | IFN-γ (pg/mg total protein) | TNF-α (ng/mg total protein) |
|---|---|---|---|---|
| CsA group | 3.91 ± 0.31# | 15.75 ± 4.67# | 59.15 ± 9.41# | 4.73 ± 0.17* |
| compound 1 group | 6.06 ± 0.67# | 46.00 ± 12.82* | 108.86 ± 12.98* | 3.72 ± 0.25** | mean ± SEM, #p < 0.001 (vs. control group)
*p < 0.05 (vs. control group)
**p < 0.01 (vs. CsA group)

The IL-2 concentration known to relate to T cell proliferation was suppressed in both the CsA group and compound 1 group. However, the degree of IL-2 suppression in the compound 1 group was lower than that in the CsA group. The concentration of IFN-γ capable of inhibiting virus replication (Jpn. Circ. J. 51:661-664, 1987) was markedly reduced in the CsA group, but reduced by a smaller degree in the compound 1 group. Similarly, the concentration of Th1 (1 type helper T cell)-specific cytokine IL-12 was markedly reduced in the CsA group, but less so in the compound 1 group. Conversely, one of the inflammatory cytokines, TNF-α, showed an increase in the concentration in the CsA group as compared to the control group, but no effect was found in the compound 1 group.

(5) Intracardiac Nitric Oxide (NO) Assay

The intracardiac NO content was measured using the same supernatant as used for the cytokine assay according to a modified method of Griess method (J. Am. Coll. Cardiol. 33:1400-1407, 1999; Anal. Biochem. 224:502-508, 1995). In brief, the supernatant or standard nitrite (50 μl) was mixed with 10 μM βNADPH (10 μl). Thereto was added a master mix previously mixed (500 μM glucose-6-phosphate, 160 U/l glucose-6-phosphate dehydrogenase, 80 U/l nitrate reductase, 0.2 mM phosphate buffer)(40 μl), and the mixture was incubated at 20° C. for 45 min. 1% Sulfanilamide (50 μl) in 5% $H_3PO_4$ and 0.1% naphthylethylenediamine dihydrochloride (50 μl) were further added, and the mixture was incubated at 20° C. for 10 min. Optical density at 540 nm was measured using a microplate reader. The nitrite concentration of each sample was calculated based on the standard product. The measurement of each sample and the standard product was done in duplicate. The intracardiac NO content was determined by dividing each nitrite concentration by the total protein concentration of each supernatant and expressed in μM/mg total protein. The statistical analysis was conducted by one way ANOVA and Fisher's protected least significant difference test.

Results

Figure 9:
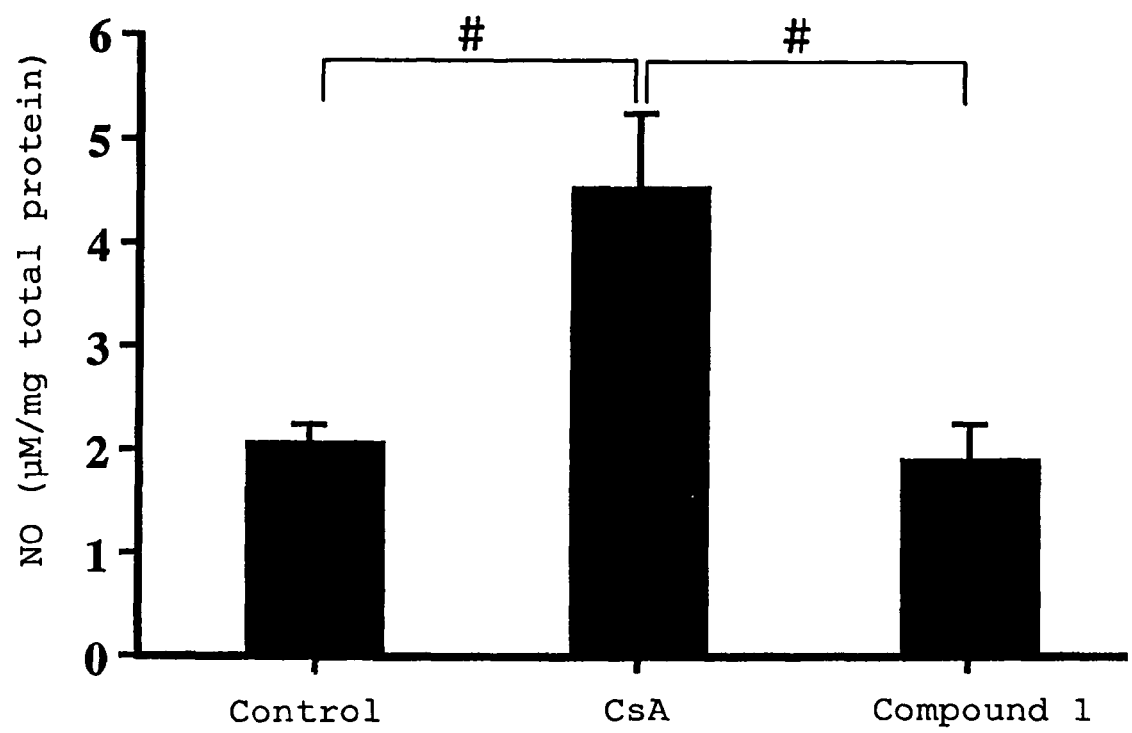
FIG. 9 is a graph showing the results of the intracardiac NO assay in Experimental Example 2.

The results are shown in FIG. 9 and Table 5.

TABLE 5

|  | NO content (μM/mg total protein) |
|---|---|
| control group | 2.07 ± 0.20# |
| CsA group | 4.56 ± 0.68 |
| compound 1 group | 1.91 ± 0.34# | mean ± SEM, #p < 0.001 (vs. CsA group)

The CsA group showed a significant increase in the intracardiac NO content as compared to the control group, but the compound 1 group showed no significant difference from the control group.

To sum up the above-mentioned results, the expression of IL-2, IL-12 and IFN-γ in the heart was suppressed in both the compound 1 group and the CsA group as compared to the control group, but the level of suppression was low in the compound 1 group. TNF-α and NO increased significantly in the CsA group, but the compound 1 group showed no significant difference from the control group. IL-2 is involved in the T cell proliferation and has an activity to induce production of IFN-γ from T cell and NK cell. A Th1 specific cytokine, IL-12, induces production of IFN-γ from T cell and NK cell. IFN-γ shows a virus growth inhibitory activity by the activation of macrophage. Thus, the above-mentioned results revealing that the level of inhibition of the production of IL-2, IL-12 and IFN-γ is higher in the CsA group than in the compound 1 group is in line with the results of the above-mentioned (3) wherein CsA increased virus replication but the compound 1 did not have such effect. In addition, an inflammatory cytokine, TNF-α, has a cytotoxic activity and NO is known to cause injury of cardiac muscle. From the above-mentioned results, it was clarified that CsA increased TNF-α and NO, but compound 1 did not. Therefore, compound 1 is effective for the amelioration of the viral cytotoxicity.

The above results reveal that compound 1 [2-amino-2-(2-(4-octylphenyl)ethyl)propane-1,3-diol hydrochloride] is effective for the treatment of viral myocarditis, without inducing virus replication.

Immunosuppressants such as cyclosporin and the like are used for the immunotherapy after organ or bone marrow transplantation. Its use for this end is problematic in that it causes severe infection due to the virus such as cytomegalovirus and the like. From the results of the above-mentioned tests, 2-amino-2-(2-(4-octylphenyl)ethyl)propane-1,3-diol of the present invention does not have, unlike conventional immunosuppressants, an effect of virus growth induction. Therefore, it is associated with an extremely small possibility of inducing virus (e.g., cytomegalovirus) infections even during the immunotherapy after organ or bone marrow transplantation.

Formulation Example (1) Tablet

Tablets having the following composition and containing compound 1 are produced.

| compound 1 | 1 mg |
|---|---|
| lactose | 90 mg |
| crystalline cellulose | 25 mg |
| magnesium stearate | 4 mg |

(2) Soft Capsule (Per Capsule)

| | |
|---|---|
| compound 1 | 30 mg |
| polyethylene glycol 300 | 300 mg |
| polysorbate 80 | 20 mg |

Production Method

Polyethylene glycol 300 and polysorbate 80 are added to compound 1 and the mixture is filled in a soft capsule.

(3) Injection (Per Ampoule, 10 ml)

| | | |
|---|---|---|
| compound 1 | 0.3% | (30 mg) |
| polyethylene glycol 300 | 20% | (2 g) |
| ethanol | 60% | (6 g) |

The total amount is adjusted to 10 ml with distilled water for injection.

Production Method

Ethanol and polyethylene glycol 300 are added to compound 1 for dissolution, and distilled water for injection is added to make the total amount 10 ml, whereby an injection containing 30 mg of compound 1 per ampoule is obtained.

INDUSTRIAL APPLICABILITY

According to the present invention, administration of 2-amino-2-(2-(4-octylphenyl)ethyl)propane-1,3-diol or a pharmacologically acceptable salt thereof is effective against cytotoxicity caused by virus, is therapeutically effective against viral myocarditis or viral diseases induced by viral myocarditis, and is also effective for the prophylaxis of these diseases.

This application is based on patent application No. 185297/1999 filed in Japan, the contents of which are hereby incorporated by reference.

What is claimed is:

1. A method for the prophylaxis or treatment of viral myocarditis other than viral myocarditis caused by picornavirus without inducing virus replication, which comprises administering an effective amount of 2-amino-2-(2-(4-octylphenyl)ethyl)propane-1,3-diol or a pharmacologically acceptable salt thereof to a patient in need thereof.

2. The method of claim 1, wherein the viral myocarditis other than viral myocarditis caused by picornavirus is caused by RNA virus or hepatitis virus.

3. The method of claim 2, wherein the RNA virus is orthomyxovirus.

4. A method for the prophylaxis or treatment of viral myocarditis other than viral myocarditis caused by picornavirus without inducing virus replication, which comprises administering an effective amount of 2-amino-2-(2-(4-octylphenyl)ethyl)propane-1,3-diol hydrochloride to a patient in need thereof.

* * * * *